US008718769B2

(12) United States Patent
Hilpisch et al.

(10) Patent No.: US 8,718,769 B2
(45) Date of Patent: May 6, 2014

(54) MONITORING VENTRICULAR CAPTURE OF APPLIED STIMULATION USING SENSED VENTRICULAR PRESSURES

(75) Inventors: Kathryn Hilpisch, St. Paul, MN (US); Barbro Maria Louise Kjellstrom, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1046 days.

(21) Appl. No.: 12/259,041

(22) Filed: Oct. 27, 2008

(65) Prior Publication Data
US 2010/0106213 A1 Apr. 29, 2010

(51) Int. Cl.
*A61N 1/37* (2006.01)

(52) U.S. Cl.
USPC .......................................................... 607/28

(58) Field of Classification Search
USPC .................................................. 607/4–28, 62
See application file for complete search history.

(56) References Cited

U.S. PATENT DOCUMENTS

| | | | |
|---|---|---|---|
| 4,374,382 A | 2/1983 | Markowitz | |
| 5,105,810 A | 4/1992 | Collins et al. | |
| 5,117,824 A | 6/1992 | Keimel et al. | |
| 5,320,643 A | 6/1994 | Roline et al. | |
| 5,545,186 A | 8/1996 | Olson et al. | |
| 5,702,427 A | 12/1997 | Ecker et al. | |
| 5,755,736 A | 5/1998 | Gillberg et al. | |
| 6,792,308 B2 | 9/2004 | Corbucci | |
| 6,937,901 B2 | 8/2005 | Zhu et al. | |
| 6,986,741 B2 | 1/2006 | Poliac et al. | |
| 7,058,450 B2 | 6/2006 | Struble et al. | |
| 7,192,399 B2 | 3/2007 | Kjellstrom et al. | |
| 7,245,970 B2 | 7/2007 | Zhu et al. | |
| 7,257,444 B2 | 8/2007 | Spinelli et al. | |
| 7,392,088 B2 | 6/2008 | Dong et al. | |
| 2001/0049543 A1* | 12/2001 | Kroll | ................................ 607/28 |
| 2004/0260351 A1 | 12/2004 | Holmstrom et al. | |
| 2006/0095085 A1 | 5/2006 | Marcus et al. | |

(Continued)

FOREIGN PATENT DOCUMENTS

| | | |
|---|---|---|
| WO | 0110499 | 2/2001 |
| WO | 2007133130 | 11/2007 |

OTHER PUBLICATIONS

Lax, Jorge A., "Estimation of the Ejection Fraction in Patients with Myocardial Infarction Obtained from the Combined Index of Systolic and Diastolic Left Ventricular Function: A New Method", Journal of the American Society of Echocardiography, Mosby-Year Book, Inc., St. Louis, MO, US, Feb. 1, 2000, pp. 1-4.

(Continued)

*Primary Examiner* — Scott Getzow
(74) *Attorney, Agent, or Firm* — Michael C. Soldner

(57) ABSTRACT

In general, this disclosure describes techniques for monitoring ventricular capture of electrical stimulation based upon sensed ventricular pressures using an implantable medical device. One example method comprises obtaining a blood pressure signal for a first ventricle (e.g., right ventricle) of a patient, and determining whether stimulation captured a second, different ventricle (e.g., left ventricle) of the patient based upon the blood pressure signal for the first ventricle. Whether stimulation captured the second ventricle may be determined based on at least one value of a myocardial performance index that is determined based upon the blood pressure signal for the first ventricle. If a loss of capture is identified, the method may further comprise providing a warning signal and/or providing a therapy adjustment signal to adjust the electrical stimulation that is provided to the second ventricle.

43 Claims, 10 Drawing Sheets

(56) References Cited

U.S. PATENT DOCUMENTS

| | | |
|---|---|---|
| 2006/0155338 A1 | 7/2006 | Mongeon et al. |
| 2006/0167514 A1 | 7/2006 | Kjellstrom et al. |
| 2007/0276446 A1 | 11/2007 | Spinelli et al. |
| 2008/0015650 A1 | 1/2008 | Zhu et al. |
| 2008/0234771 A1 | 9/2008 | Chinchoy et al. |

OTHER PUBLICATIONS (PCT/US2009/059153) PCT Notification of Transmittal of the International Search Report and the Written Opinion of the International Searching Authority.

* cited by examiner

MONITORING VENTRICULAR CAPTURE OF APPLIED STIMULATION USING SENSED VENTRICULAR PRESSURES

TECHNICAL FIELD

This disclosure relates to medical devices and, more particularly, to medical devices that deliver stimulation and monitor physiological parameters.

BACKGROUND

Cardiac resynchronization therapy (CRT) may include delivering pacing stimuli to both ventricles, or to one ventricle, with the desired result of a coordinated mechanical contraction and ejection of blood from the ventricles to, for example, alleviate symptoms of congestive heart failure (CHF). However, due to a number of factors, such pacing may not always effectively provide CRT. For example, varying capture thresholds, pacing lead and/or electrode migration or dislodgement, or time required for appropriate signal processing may all be factors that affect the ability of pacing to effectively provide CRT to a patient.

When delivering CRT, such as by applying bi-ventricular stimulation, the confirmation that pacing stimuli have captured each paced ventricle is important in determining whether the desired benefits of CRT are, in fact, delivered to a patient. Some CRT devices incorporate bi-ventricular pacing technology with synchronized pacing in the right and left ventricles. Since the devices are implanted essentially to provide continuous bi-ventricular pacing therapy, it is important that pacing pulse stimuli cause an evoked response in each ventricle (i.e., that the stimuli capture, and cause contraction of, the ventricles).

SUMMARY

In general, this disclosure describes techniques for monitoring ventricular stimulation capture based upon sensed ventricular pressures. For example, an implantable medical device may be coupled to a lead that is inserted into one ventricle of a patient (e.g., the right ventricle). The lead may include a pressure sensor, such that the device is capable of continuously monitoring the pressure within the ventricle. Based upon the pressure measurements and any corresponding calculations, the device is capable of monitoring the capture of electrical stimulation applied to another ventricle (e.g., left ventricle). A lead coupled to the device may be inserted into the other ventricle (or into a vessel that is on the other ventricle). In some examples, the device may continually estimate, or calculate, a value of a myocardial performance index based upon sensed pressure measurements and/or corresponding timing intervals. In such examples, the device may detect a loss of ventricular capture based upon detection of changes in the values of the myocardial performance index.

One example method comprises obtaining a blood pressure signal for a first ventricle (e.g., right ventricle) of a patient, and determining whether stimulation captured a second, different ventricle (e.g., left ventricle) of the patient based upon the blood pressure signal for the first ventricle. Whether stimulation captured the second ventricle may be determined based on at least one value of a myocardial performance index that is determined based upon the blood pressure signal for the first ventricle. If a loss of capture is identified, the method may further comprise providing a warning signal and/or providing a therapy adjustment signal to adjust the electrical stimulation that is provided to the second ventricle.

One example system comprises a processor configured to obtain a blood pressure signal for a first ventricle of a patient, wherein the processor is further configured to determine whether electrical stimulation captured a second, different ventricle of the patient based upon the blood pressure signal for the first ventricle.

One example implantable medical device comprises a module configured to obtain a blood pressure signal for a first ventricle of a patient from a sensor, a stimulation generator configured to deliver electrical stimulation to a second, different ventricle of the patient, and a processor configured to determine whether the electrical stimulation captured the second ventricle of the patient based upon the blood pressure signal for the first ventricle.

One example computer-readable medium comprises instructions for causing one or more processors to obtain a blood pressure signal for a first ventricle of a patient, and to determine whether electrical stimulation captured a second, different ventricle of the patient based upon the blood pressure signal for the first ventricle.

The details of one or more examples are set forth in the accompanying drawings and the description below. Other features, objects, and advantages will be apparent from the description and drawings, and from the claims.

DETAILED DESCRIPTION

Figure 1:
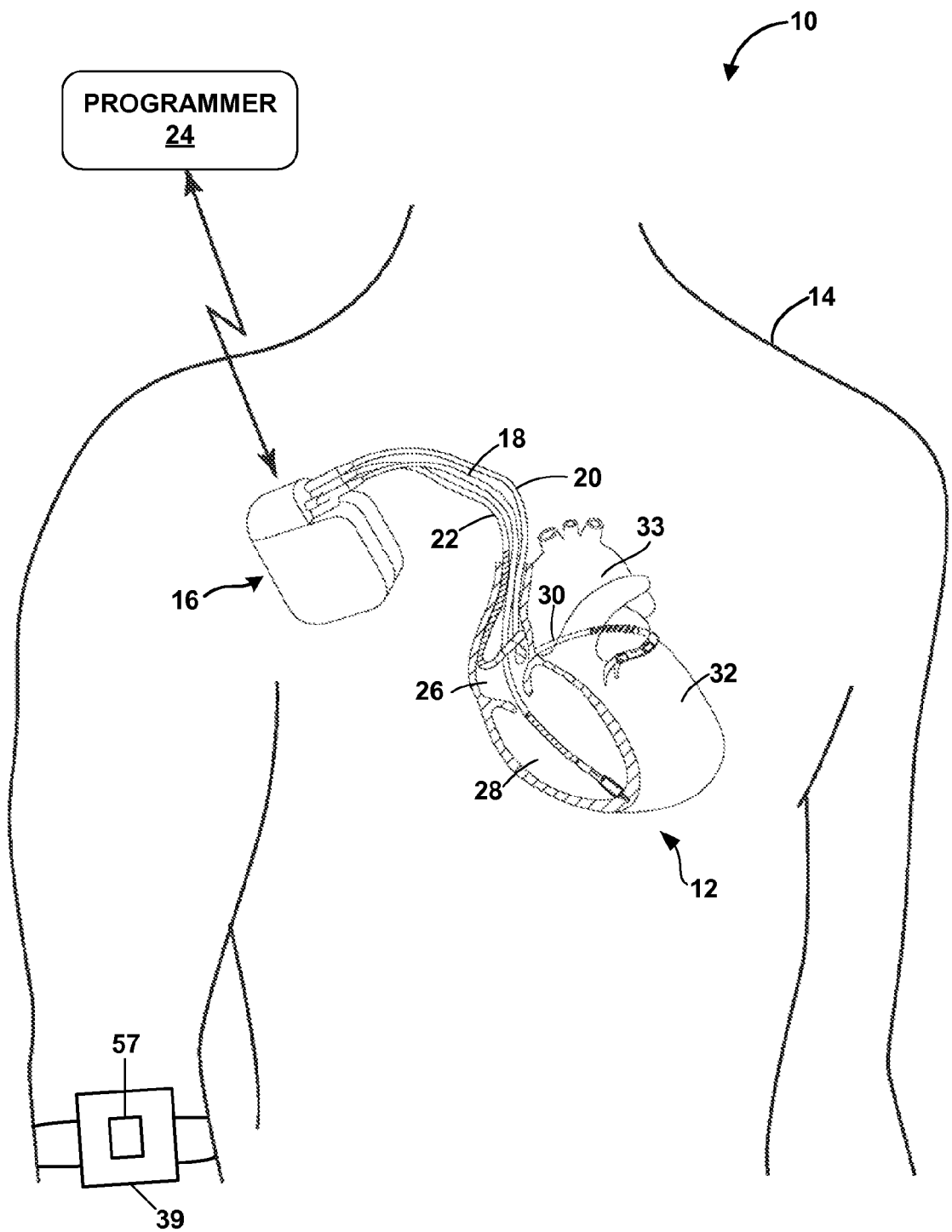
FIG. 1 is a conceptual diagram illustrating an example therapy system that may be used to monitor a myocardial performance index of a patient and/or provide therapy to the patient.

FIG. 1 is a conceptual diagram illustrating an example therapy system 10 that may be used to monitor a myocardial performance index of patient 14 and/or provide therapy to heart 12 of patient 14. Patient 14 ordinarily, but not necessarily, will be a human. Therapy system 10 includes IMD 16, which is coupled to leads 18, 20, and 22, atmospheric pressure reference monitor 39 (which may include a telemetry function and a timepiece function 57), and programmer 24. IMD 16 may be, for example, an implantable pacemaker, cardioverter, and/or defibrillator that provides electrical signals to heart 12 via electrodes coupled to one or more of leads 18, 20, and 22.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, temperature, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

As shown in FIG. 1, patient 14 is also provided with atmospheric pressure reference monitor 39 to record atmospheric pressure values. Atmospheric pressure reference monitor 39 is schematically depicted as worn on the wrist of patient 14 with an optional timepiece function 57, but it may take other portable configurations so that it can accompany patient 14 during a daily routine. Atmospheric pressure reference monitor 39 may include a memory to store recorded pressure readings. In various cases, atmospheric pressure reference monitor 39 may not be needed by patient 14.

In some cases, atmospheric pressure reference monitor 39 includes a telemetry module, such that it may be able to wirelessly communicate with programmer 24. In some cases, a direct cable or plug-in connection can be made between ports of atmospheric pressure reference monitor 39 and programmer 24 when atmospheric pressure data is to be read from memory in atmospheric pressure reference monitor 39. The storage of absolute blood pressure data and ambient pressure data within atmospheric pressure reference monitor 39 may continue for a period of days, and the data may be periodically transmitted to programmer 24 upon request by programmer 24. In some cases, atmospheric pressure reference monitor 39 may periodically initiate transfer of data to programmer 24. However, as noted above, in various cases, atmospheric pressure reference monitor 39 may not be needed or used, particular when differences only in relative pressure measurements are obtained or analyzed.

In one example, IMD 16 is capable of monitoring ventricular stimulation capture based upon sensed ventricular pressures, as will be described in more detail below. For example, IMD 16 may be capable of continuously monitoring blood pressure signals within one ventricle (e.g., within right ventricle 28). Based upon the pressure measurements and any corresponding calculations, IMD 16 is capable of monitoring the capture of electrical stimulation applied to another ventricle (e.g., left ventricle 32).

In some cases, IMD 16 may continually estimate, or calculate, a value of a myocardial performance index based upon sensed pressure measurements and/or corresponding timing intervals. IMD 16 is capable of detecting a loss of ventricular stimulation capture upon detection of changes in the value of the myocardial performance index over time. IMD 16 may, in some cases, provide a warning signal and/or provide a therapy adjustment signal to adjust the amount or type of electrical stimulation that is provided to the other ventricle (e.g., left ventricle) when IMD 16 has detected a loss of ventricular stimulation capture based upon such changes in the value of the myocardial performance index.

Figure 2:
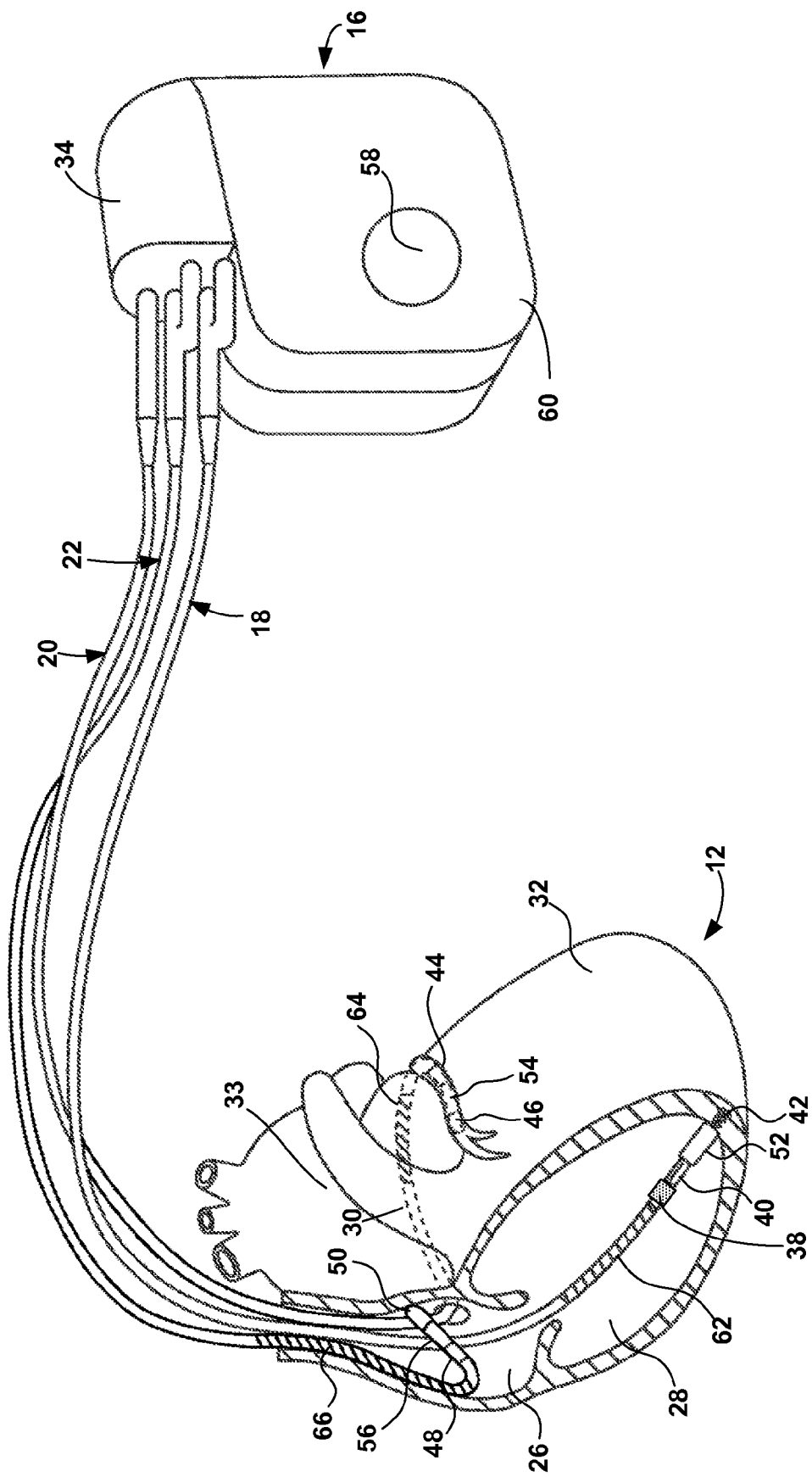
FIG. 2 is a conceptual diagram illustrating the implantable medical device (IMD) and leads of the therapy system shown in FIG. 1 in greater detail, according to one embodiment.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 38 may respond to an absolute pressure inside right ventricle 28, and may be, for example, a capacitive or piezoelectric absolute pressure sensor. In other examples, pressure sensor 38 may be positioned within other regions of heart 12 and may monitor pressure within one or more of the other regions of heart 12, or may be positioned elsewhere within or proximate to the cardiovascular system of patient 14 (FIG. 1) to monitor cardiovascular pressure associated with mechanical contraction of the heart.

Electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As described in further detail with reference to FIG. 4, housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. In some examples, IMD 16 may sense electrical signals attendant to the depolarization and repolarization of heart 12 via any combination of electrodes 40, 42, 44, 46, 48, 50, 58, 62, 64 and 66.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes. In addition, in some examples, pressure sensor 38 may be self-contained device that is implanted within heart 12, such as within the septum separating right ventricle 28 from left ventricle 32, or the septum separating right atrium 26 from left atrium 33. In such an example, pressure sensor 38 may wirelessly communicate with IMD 16.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIGS. 1 and 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. As another example, other examples of therapy systems may include a single lead that extends from IMD 16 into right atrium 26 or right ventricle 28, or two leads that extend into a respective one of the right ventricle 26 and right atrium 28. An example of this type of therapy system is shown in FIG. 3.

Figure 3:
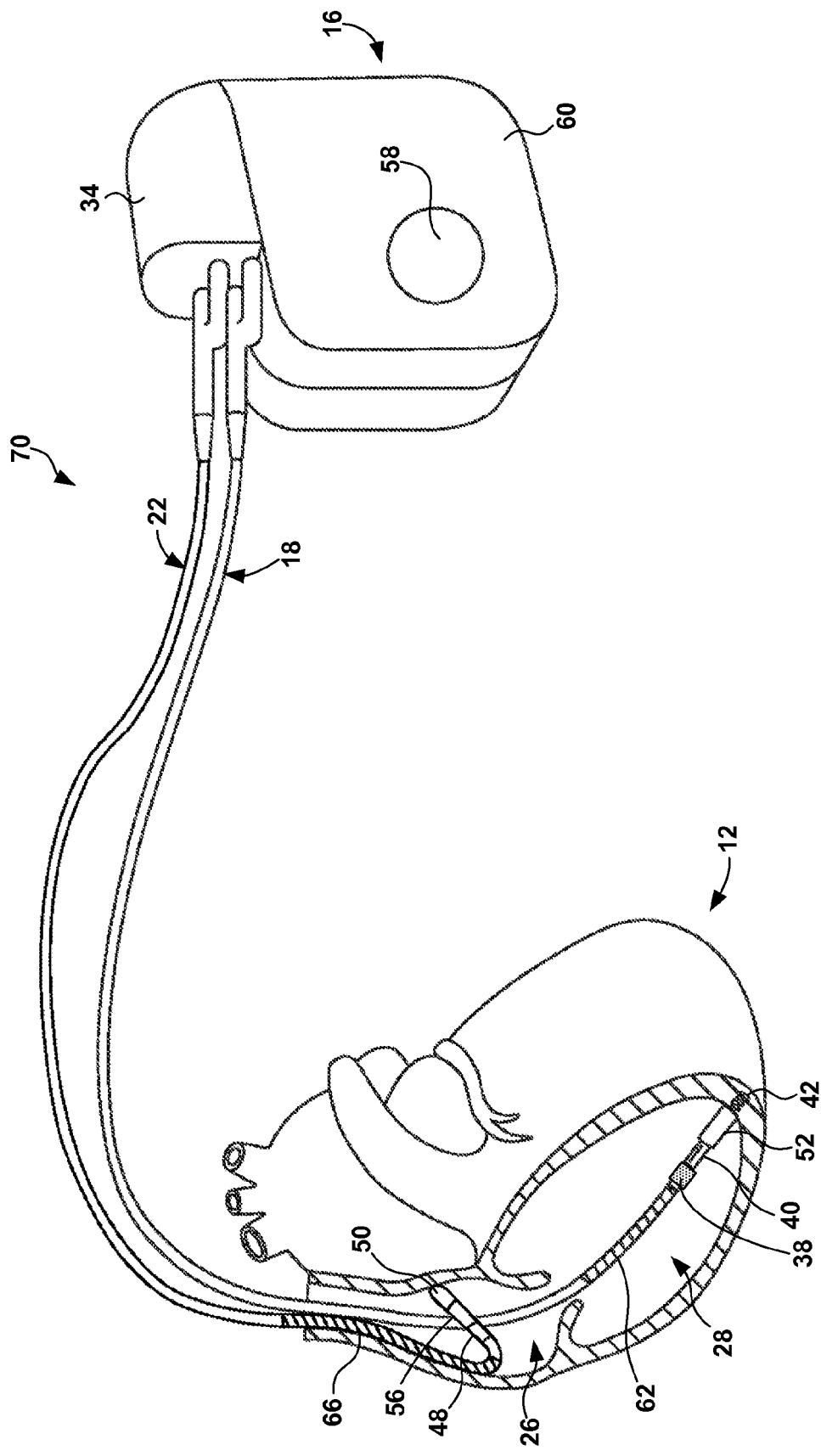
FIG. 3 is a conceptual diagram illustrating another example of a therapy system.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12.

Figure 4:
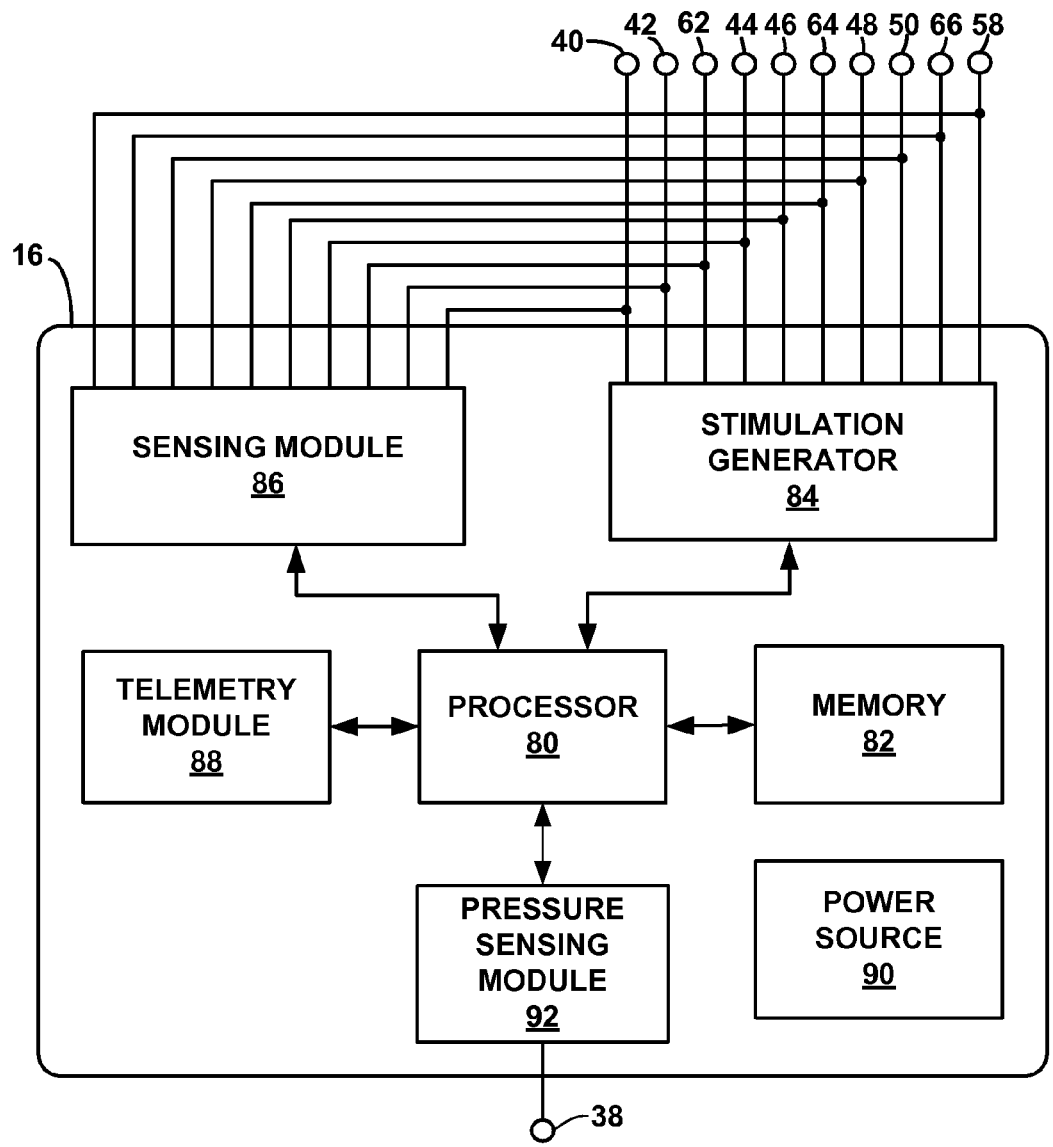
FIG. 4 is a functional block diagram of one example configuration of the IMD shown in FIGS. 1-3.

FIG. 4 is a functional block diagram of one example configuration of IMD 16, which includes processor 80, memory 82, stimulation generator 84, sensing module 86, telemetry module 88, power source 90, and pressure sensing module 92. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 in FIGS. 1 and 2 according to a selected one or more of therapy programs, which may be stored in memory 82. Specifically, processor 80 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22 in FIGS. 1 and 2, or, in the case of housing electrode 58, via an electrical conductor disposed within housing 60 in FIGS. 2 and 3 of IMD 16. Stimulation generator 84 is configured to generate and deliver electrical stimulation therapy to heart 12 in FIGS. 1 and 2. For example, stimulation generator 84 may deliver defibrillation shocks to heart 12 via at least two electrodes 58, 62, 64, 66. Stimulation generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12 in FIGS. 1 and 2, e.g., via electrogram (EGM) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprises an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12 in FIGS. 1 and 2. Another channel may include another R-wave amplifier that receives signals from electrodes 44 and 46, which are used for pacing and sensing proximate to left ventricle 32 of heart 12 in FIGS. 1 and 2. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12 in FIGS. 1 and 2. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12 in FIGS. 1 and 2

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 in FIG. 1 by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, in one embodiment, "D" indicates dual chamber, "V" indicates a ventricle, "I" indicates inhibited pacing (e.g., no pacing), "A" indicates an atrium, and "R" indicates rate response. In this embodiment, the first letter in the pacing mode indicates the chamber that is paced, the second letter indicates the chamber in which an electrical signal is sensed, and the third letter indicates the mode of response (e.g., inhibit, triggered, or dual-mode response).

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pacer timing and control module may define a blanking period, and provide signals from sensing module 86 to blank one or more channels, e.g., amplifiers, for a period during and after delivery of electrical stimulation to heart 12 in FIGS. 1 and 2. The durations of these intervals may be determined by processor 80 in response to stored data in memory 82. The pacer timing and control module of processor 80 may also determine the amplitude of the cardiac pacing pulses.

The pacer timing and control module may also be used to deliver, or provide, cardiac resynchronization therapy (CRT) using stimulation generator 84. The pacer timing and control module may provide pacing therapies with one or more pacing leads in two or more complementary chambers of the heart, such as left ventricle 32 and right ventricle 28, or left atrium 33 and right atrium 26 in FIGS. 1 and 2. Right atrium 26 and left atrium 33 are complementary because they are the upper chambers that receive blood from the lung and systemic circulation and transfer it to the ventricles. Right ventricle 28 and left ventricle 32 are complementary chambers because they receive blood from the atria and pump the blood to the lung and systemic circulation. In a heart of a healthy patient, complementary chambers activate at approximately the same time. In a heart of a patient suffering from certain conditions, such as right or left heart failure, complementary chambers may activate at different times.

In response to a sensed or paced event, the pacer timing and control module may deliver pacing pulses or stimulations to complementary chambers of the heart, such as to left ventricle 32 and right ventricle 28 (e.g., bi-ventricular pacing) in FIGS. 1 and 2. The pacing pulses may be delivered in a coordinated, or synchronized, fashion. These pacing pulses may be, but need not be, delivered simultaneously. The pacer timing and control module may provide CRT by synchronizing ventricular and/or atrial contractions. In some cases, the pacer timing and control module may deliver pacing pulses to complementary chambers at different times in order to achieve synchronization, or resynchronization.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12 in FIGS. 1 and 2. Processor 80 may reset the escape interval counters upon the generation of pacing pulses by stimulation generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 80 may identify the presence of a tachyarrhythmia episode, such as a ventricular fibrillation episode, a ventricular tachycardia episode, or a non-sustained tachycardia (NST) episode.

In some cases, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 in FIGS. 1 and 2 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. are incorporated herein by reference in their entireties. However, other arrhythmia detection methodologies may also be employed by processor 80 in other examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by stimulation generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation pulses to heart 12 in FIGS. 1 and 2, stimulation generator 84 may include a high voltage charge circuit and a high voltage output circuit. If IMD 16 is configured to generate and deliver pacing pulses to heart 12, stimulation generator 84 may include a low voltage charge circuit and a low voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of stimulation generator 84.

Pressure sensing module 92 receives pressure signals from pressure sensor 38. Pressure sensor 38 may generate pressure signals itself or may modulate pressure signals conducted through lead 18 in FIGS. 1, 2 and 3. The pressure signals are a function of the fluid pressure at the site where pressure sensor 38 is disposed. In the example shown in FIGS. 2 and 3, pressure sensor 38 is disposed in right ventricle 28 of heart 12. Pressure sensing module 92 may receive, monitor, and analyze the pressure signals, as will be described in more detail below. An example of a suitable pressure sensing module 92 includes the Chronicle Implantable Hemodynamic Monitor manufactured by Medtronic, Inc. of Minneapolis, Minn.

Pressures sensing module 92, or, alternatively, processor 80, may measure, observe, or derive different pressure characteristics from the signals generated by pressure sensor 38. For example, in embodiments when pressure sensor 38 generates a signal indicative of the pressure within right ventricle 28, pressure sensing module 92 may measure the right ventricular systolic pressure by observing a peak pressure in right ventricle 28, and the right ventricular diastolic pressure may be measured as the pressure in right ventricle 28 at the time of the sensing of an R wave. Pulse pressure may be the difference between the right ventricular systolic pressure and the right ventricular diastolic pressure.

Another pressure characteristic that pressure sensing module 92 may measure include the right ventricular mean pressure, which is the mean pressure in right ventricle 28 during a cardiac cycle. A cardiac cycle (or "heart cycle") typically includes at least a Q-wave, an R-wave, and an S-wave. Estimated pulmonary artery diastolic pressure (EPAD) is another pressure characteristic that may be indicative of activity within heart 12 in FIGS. 1 and 2, which pressure sensing module 92 may monitor. EPAD reflects the pulmonary capillary wedge pressure, which reflects the average pressure in left atrium 33 in FIGS. 1 and 2 over a cardiac cycle, which may also be referred to as the mean left atrial pressure. EPAD may also reflect the filling pressure in the left ventricle during diastole, also called the left ventricular end diastolic pressure. Techniques for measuring EPAD is described in U.S. Pat. No. 7,058,450 to Struble et al., entitled, "ORGANIZING DATA ACCORDING TO CARDIAC RHYTHM TYPE," which issued on Jun. 6, 2006 and is incorporated herein by reference in its entirety. Again, in various examples, pressure may be measured in other chambers of heart 12, or other locations within the cardiovascular system of patient 14, such as within a pulmonary artery or vena cava.

Upon receipt of pressure signals by pressure sensing module 92 and electrical signals by sensing module 86, processor 80 is capable of deriving several hemodynamic parameters defining the operation of a ventricle (such as the right ventricle), including a peak positive and a negative dP/dt, a pre-ejection interval (PEI), a post-ejection interval (PEI2), and a systolic time interval (STI). These hemodynamic parameters may then be stored in memory 82 by processor 80 on a beat-by-beat basis, minute-to-minute basis, hour-to-hour basis, or on some other basis.

Figure 7:
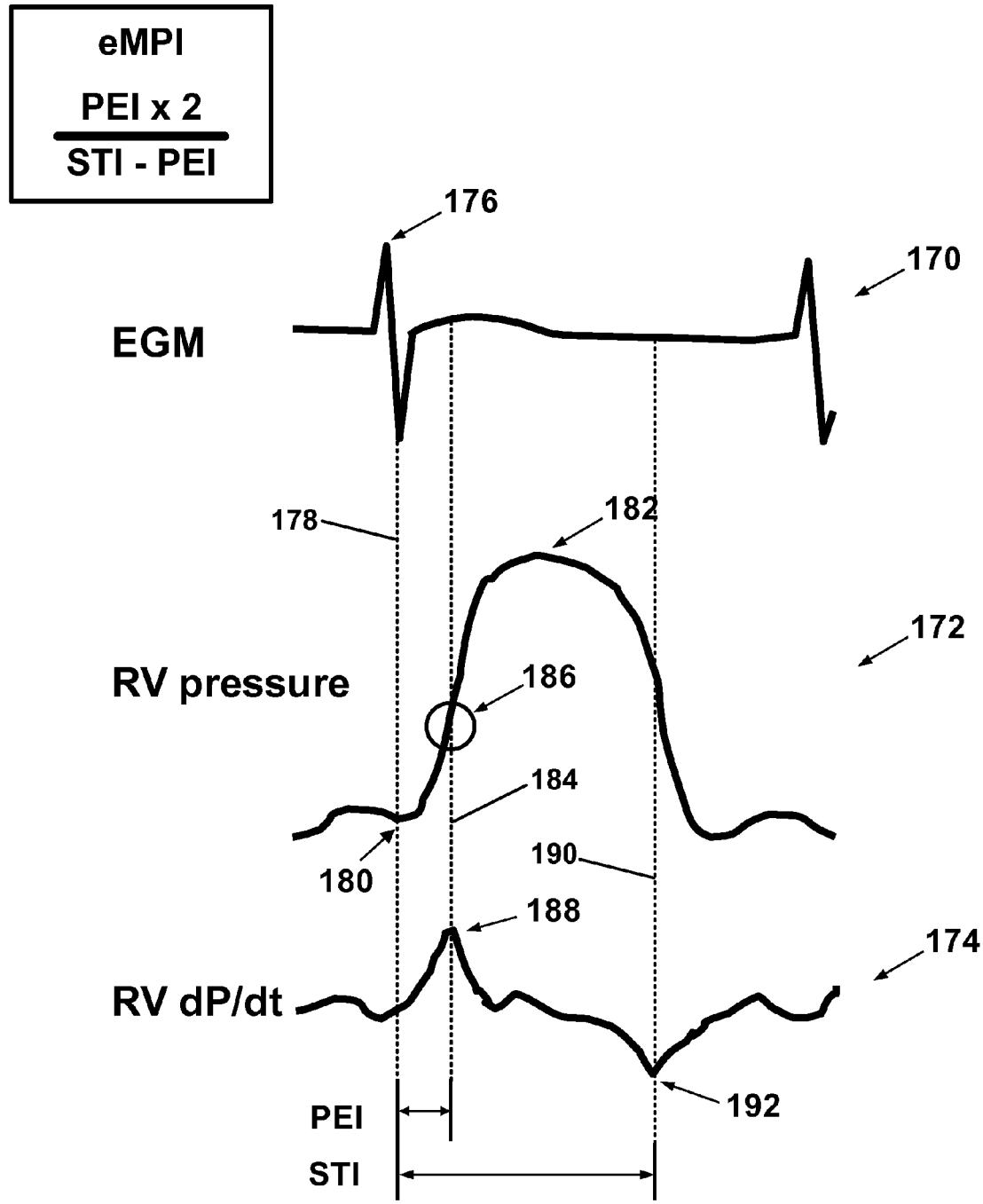
FIG. 7 is a timing diagram providing an overview of an example mode of operation of the IMD shown in FIGS. 1-4 to determine an estimate of a myocardial performance index.

Processor 80 may use these hemodynamic parameters to further derive an estimated, or modified, myocardial performance index (eMPI) as a function of these hemodynamic parameters, as is described in more detail within U.S. Pat. No. 7,192,399 to Kjellstrom et al., which issued on Mar. 20, 2007 and is entitled "SYSTEM AND METHOD FOR MONITORING MYOCARDIAL PERFORMANCE USING SENSED VENTRICULAR PRESSURES," the entire content of which is incorporated herein by reference. For instance, the eMPI may be derived as a function of the pre-ejection interval (PEI) and the systolic time interval (STI). The difference (STI−PEI) may be referred to as the ejection interval. In one example, such as shown in FIG. 7, the eMPI may be derived as:

$$eMPI=PEI \times A/(STI-PEI),$$

where A is a numeric factor. In some cases, numeric factor A may be determined such that the product (PEI×A) approximates a sum of the two isovolumetric intervals. For example, numeric factor A may equal two, such that the eMPI is determined as:

$$eMPI=PEI \times 2/(STI-PEI).$$

Figure 8:
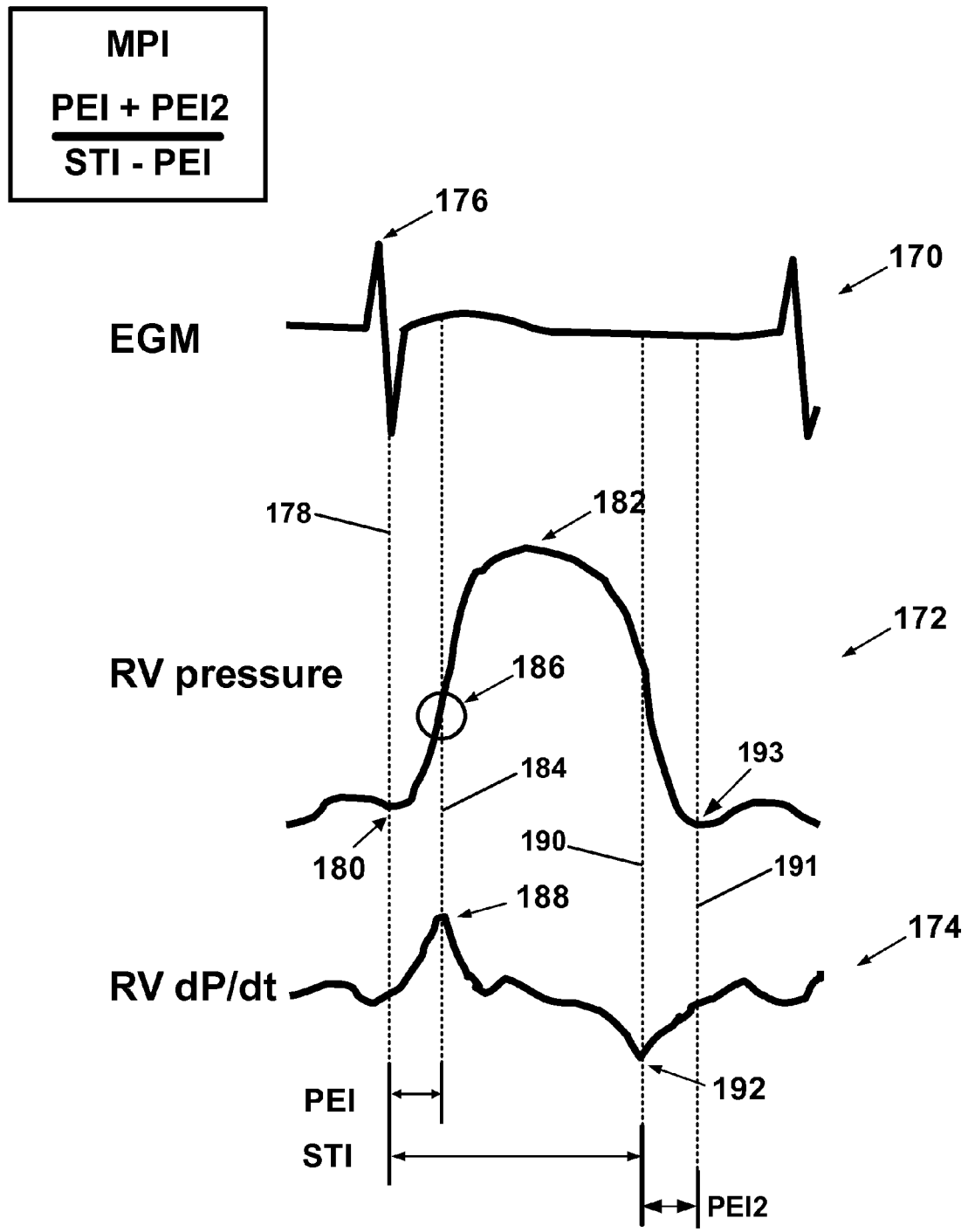
FIG. 8 is a timing diagram providing an overview of another example mode of operation of the IMD shown in FIGS. 1-4 to determine a value of a myocardial performance index.

In some cases, numeric factor A may be determined to compensate for variations caused in the pressure signal, such as may be caused by transmitted pacing signals. If processor 80 is capable of deriving the post-ejection interval (PEI2) from the processed pressure signal, as will be described in further detail below, the myocardial performance index (MPI) need not be estimated, but may be calculated (such as shown in the example of FIG. 8) as:

$$MPI=(PEI+PEI2)/(STI-PEI).$$

By chronically monitoring a patient's eMPI or MPI, physicians may be able to ascertain an effect of various therapies on patient 14 in FIG. 1, with a decrease in eMPI or MPI indicating a positive effect of the therapy on the cardiac performance of patient 14.

For certain analyses, the eMPI can be normalized using heart rate and/or right ventricular pressure for pre-load adjustments. For example, the eMPI can be normalized for heart rate (HR) by monitoring an index derived by multiplying the eMPI by a factor related to the heart rate of patient 14 in FIG. 1. One such heart-rate normalized index is an (eMPI× HR) index.

In some embodiments, processor 80 next compares the myocardial performance index (eMPI or MPI) to a myocardial performance index threshold for patient 14 in FIG. 1, the threshold being stored in memory 82. The myocardial performance index threshold of patient 14 may be determined during an initializing period in which patient 14 is monitored to establish a baseline, or normal, value for his/her myocardial performance index. The threshold can then be set as a value greater than the baseline, for example, a value 5%-50% greater than the baseline value.

Any increases in the myocardial performance index above the threshold may be a predictor of diminished cardiac function and/or worsening heart condition, such that additional medical intervention may be warranted for patient 14 in FIG. 1. Thus, in one example, processor 80 may instruct telemetry module 88 to transmit an alert to medical personnel whenever the myocardial performance index rises above the myocardial performance index threshold. For example, telemetry module 88 may transmit information related to the myocardial performance index, or an alert, to programmer 24 in FIGS. 1 and 2, or to another device external to patient 14, that may display the information or alert to a clinician. In some cases, an alert may be generated within IMD 16.

In some instances, processor 80, upon detection of the myocardial performance index rising above the myocardial performance index threshold, may automatically provide a therapy control signal to stimulation generator 84 to adjust or titrate any of various therapies being administered to patient 14 in FIGS. 1 and 2. In one example, the therapy control signal may be provided as a function of the myocardial performance index, regardless of whether the myocardial performance index has risen above the myocardial performance index threshold.

The derivation of the myocardial performance index may also be useful in the optimization of the pacemaker settings for patient 14 in FIGS. 1 and 2. In particular, a set of pacing settings can be selected based upon the monitored effect of various pacing settings of the pacemaker of patient 14 on the myocardial performance index.

In one example, IMD 16 is capable of monitoring ventricular stimulation capture based upon sensed ventricular blood pressure signals from pressure sensing module 92, as is described in more detail below. For example, IMD 16 may use pressure sensing module 92 to continuously monitor blood pressure signals within one ventricle (e.g., within right ventricle 28 in FIGS. 1 and 2). Based upon the pressure measurements and any corresponding calculations, IMD 16 (or other external devices, such as programmer 24 or other device, as described in more detail below with reference to FIG. 6) is capable of monitoring the capture of electrical stimulation applied to another ventricle (e.g., left ventricle 32 in FIGS. 1 and 2). In some cases, IMD 16 may use processor 80 to continually estimate, or calculate, a value of a myocardial performance index based upon sensed pressure measurements and/or corresponding timing intervals. IMD 16 is capable of detecting a loss of ventricular stimulation capture upon detection of changes in the value of the myocardial performance index over time. IMD 16 may, in some cases, provide a warning signal and/or provide a therapy adjustment signal to adjust the amount or type of electrical stimulation that is provided to the other ventricle (e.g., left ventricle) of patient 14 in FIGS. 1 and 2 by stimulation generator 84 when IMD 16 has detected a loss of ventricular stimulation capture based upon such changes in the value of the myocardial performance index.

Telemetry module 88 includes any suitable hardware, firmware, software or any combination thereof for wirelessly communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24 in FIG. 1. Programmer 24 may interrogate IMD 16 to receive the heart signals. Processor 80 may store heart signals within memory 82, and retrieve stored heart signals from memory 82. Processor 80 may also generate and store marker codes indicative of different cardiac episodes that sensing module 86 and pressure sensing module 92 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly or longer basis.

Although FIG. 4 illustrates pressure sensing module 92 as a separate component from processor 80, in other examples, processor 80 may include the functionality attributed to pressure sensing module 92 herein. For example, pressure sensing module 92 shown in FIG. 4 may include software executed by processor 80. If pressure sensing module 92 includes firmware or hardware, pressure sensing module 92 may be a separate one of the one or more processors 80 or may be a part of a multifunction processor. As previously described, processor 80 may comprise one or more processors.

Further, in other examples of therapy system 10 in FIGS. 1 and 2, pressure sensing module 92 may be separate from IMD 16. That is, although pressure sensing module 92 is shown in FIG. 4 to be incorporated within housing 60 of IMD 16 along with other components such as processor 80, stimulation generator 84 and sensing module 86, in other examples, pressure sensing module 92 may be enclosed in a separate housing. The stand-alone pressure sensing module that is enclosed in a separate housing from IMD 16 housing 60 may be mechanically coupled to IMD 16 or may be mechanically decoupled from IMD 16. For example, in some examples, pressure sensing module 92 and pressure sensor 38 may be implanted within patient 14 at a separate location from IMD 16 and leads 18, 20, 22. Pressure sensing module 92 may communicate with IMD 16 via a wired connection or via wireless communication techniques, such as RF telemetry.

In yet other examples of therapy system 10 (FIGS. 1 and 2), pressure sensing module 92 may be external to patient 14 and may receive signals from an implanted pressure sensor 38 via wireless telemetry. For example, programmer 24, which may be a patient programmer or a clinician programmer, may include pressure sensing module 92. As another example, a computing device other than programmer 24 may include pressure sensing module 92. In some examples, data from pressure sensor 38 and sensing module 86 may be uploaded to a remote server from which a clinician or another user may access the data to determine whether a potential sensing integrity issue exists. An example of a remote server includes the CareLink Network, available from Medtronic, Inc. of Minneapolis, Minn. An example of a system that includes an external device, such as a server, and one or more computing devices that are coupled to IMD 16 and programmer 24 via a network is described below with respect to FIG. 6.

Figure 5:
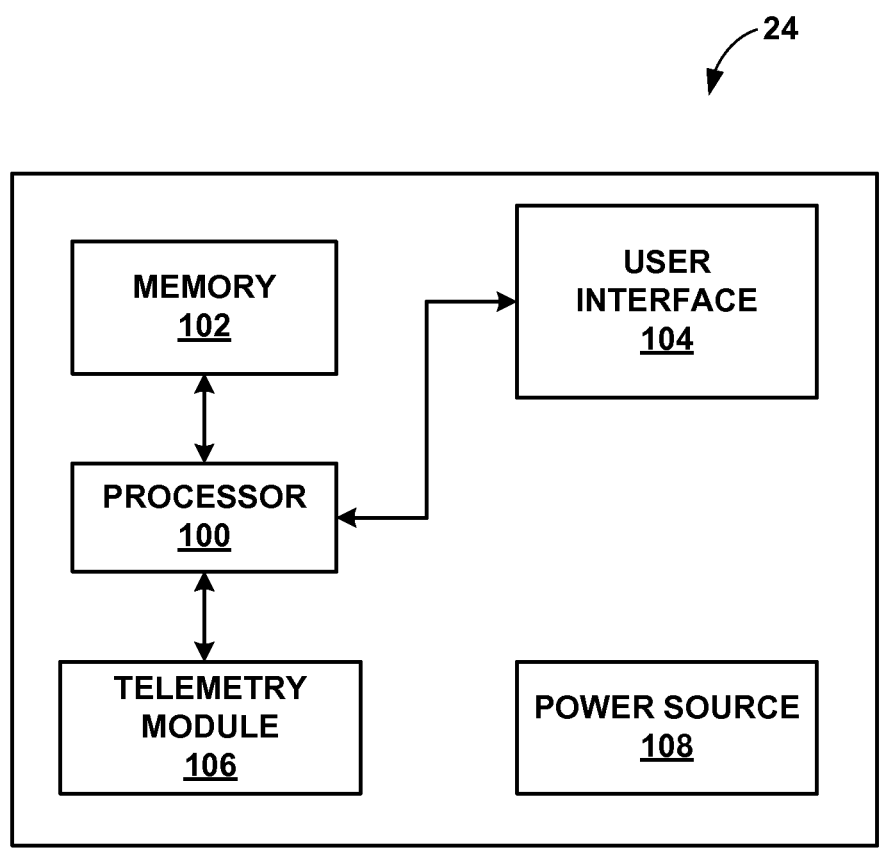
FIG. 5 is a functional block diagram of one example configuration of the programmer shown in FIG. 1.

FIG. 5 is functional block diagram of an example programmer 24. As shown in FIG. 5, programmer 24 includes processor 100, memory 102, user interface 104, telemetry module 106, and power source 108. Programmer 24 may be a dedicated hardware device with dedicated software for programming of IMD 16 (FIG. 1). Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16 (FIG. 1), such as stimulation parameter values.

Programmer 24 may communicate wirelessly with IMD 16 in FIG. 1, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over IMD 16, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Referring again to FIG. 4, processor 80 of IMD 16 may detect a tachyarrhythmia episode, such as a ventricular fibrillation, ventricular tachycardia, fast ventricular tachyarrhythmia episode, or a NST episode, based on electrical activity of heart 12 in FIGS. 1, 2 and 3 that is monitored via sensing module 86. For example, sensing module 86, with the aid of at least some of the electrodes 40, 42, 44, 46, 48, 50, 58, 62, 64, and 66 (shown in FIGS. 1-2), may generate an electrogram (EGM) signal that indicates the electrical activity. Alternatively, sensing module 86 may be coupled to sense electrodes that are separate from the stimulation electrodes that deliver electrical stimulation to heart 12, and may be coupled to one or more different leads than leads 18, 20, 22 (shown in FIGS. 1-2). The EGM signal may be indicative of the depolarization of heart 12.

For example, as previously described, in some examples, processor 80 may identify the presence of a tachyarrhythmia episode by detecting a threshold number of tachyarrhythmia events (e.g., R-R or P-P intervals having a duration less than or equal to a threshold). In some examples, processor 80 may also identify the presence of the tachyarrhythmia episode by detecting a variable coupling interval between the R-waves of the heart signal.

Pressure sensing module 92 of IMD 16 may generate a signal indicative of a cardiovascular pressure, which may be used to discriminate electrical noise from heart signals (e.g., an EGM signal). As described above, in different embodiments, pressure sensing module 92 may monitor a pressure within right atrium 26, right ventricle 28, coronary sinus 30, left atrium 33, or other regions of heart 12 (FIGS. 1 and 2). Instead or in addition to sensing a pressure within heart 12, pressure sensing module 92 may sense a pressure within the vasculature of patient 12, e.g., within an artery or a vein. Accordingly, while a pressure within right ventricle 28 is primarily referred to with reference to FIGS. 6-12, in other examples, pressure sensing module 92 may monitor a pressure within other portions of heart 12 or vasculature to help discriminate electrical noise from heart signals.

Figure 6:
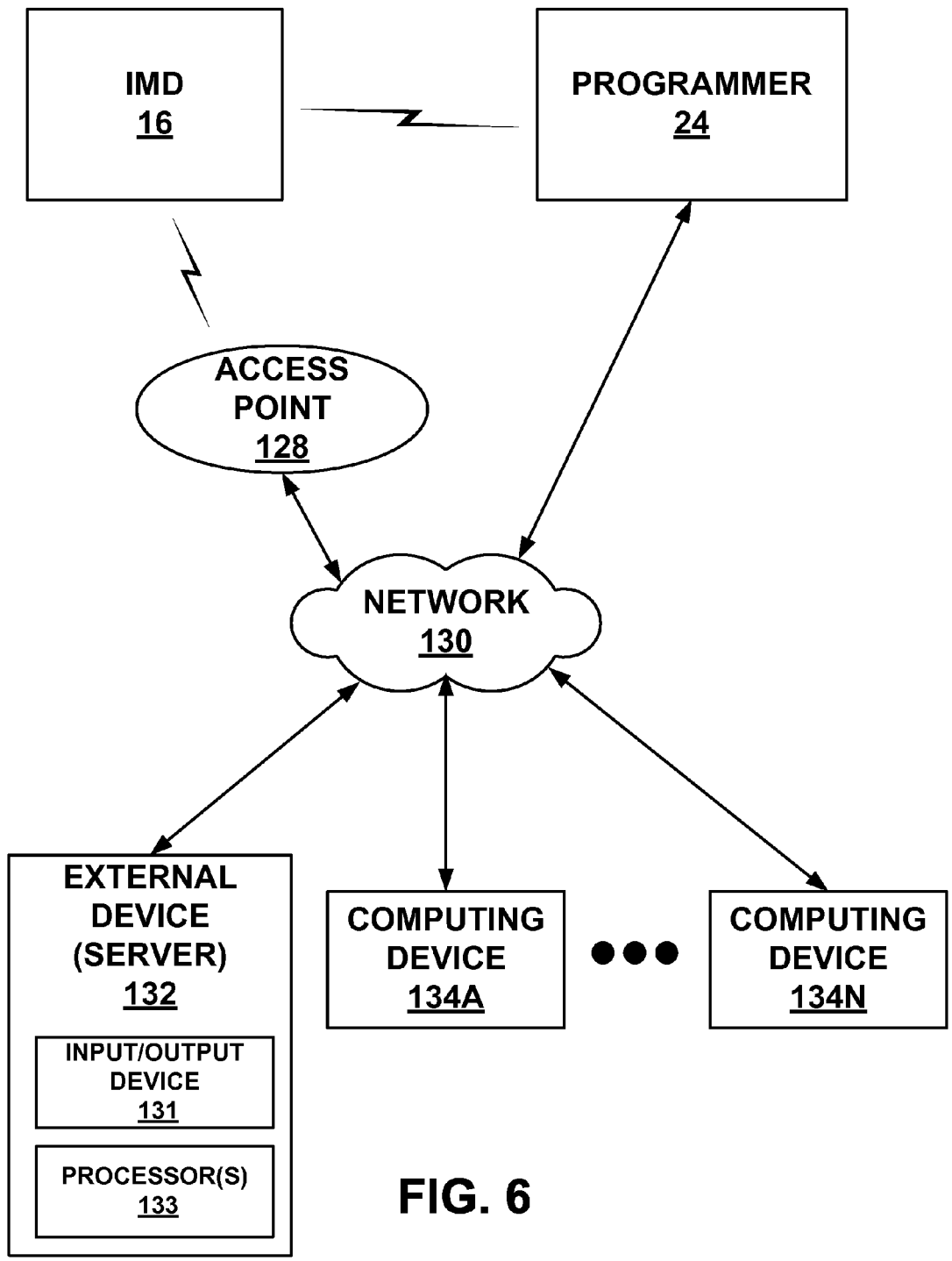
FIG. 6 is a functional block diagram illustrating an external device and one or more computing devices that may be coupled to the IMD and programmer shown in FIGS. 1-5.

FIG. 6 is a functional block diagram illustrating an external device 132, such as a server, and one or more computing devices 134A-134N that are coupled to IMD 16 and programmer 24 shown in FIG. 1 via a network 130, according to one example. In this example, IMD 16 uses its telemetry module 88 (FIG. 4) to communicate with programmer 24 via a first wireless connection, and to communication with an access point 128 via a second wireless connection. In some cases, IMD 16 may communicate with other access points, programmers, and/or computing devices (not shown) that are co-located with patient 14 (FIG. 1) via one or more wireless connections.

In the example of FIG. 6, access point 128, programmer 24, external device 132, and computing devices 134A-134N are interconnected, and able to communicate with each other, through network 130. In some cases, one or more of access point 128, programmer 24, external device 132, and computing devices 134A-134N may be coupled to network 130 through one or more wireless connections. IMD 16, programmer 24, external device 132, and computing devices 134A-134N may each comprise one or more processors, such as one or more microprocessors, DSPs, ASICs, FPGAs, programmable logic circuitry, or the like, that may perform various functions and operations, such as those described herein. In some examples, additional access points, programmers, and/or computing devices that are coupled to IMD 16 and co-located with patient 14 (not shown) may also each comprise one or more processors, such as one or more microprocessors, DSPs, ASICs, FPGAs, programmable logic circuitry, or the like, that may perform various functions and operations, such as those described herein.

Access point 128 may comprise a device that connects to network 130 via any of a variety of connections, such as telephone dial-up, digital subscriber line (DSL), or cable modem connections. In other embodiments, access point 128 may be coupled to network 130 through different forms of connections, including wired or wireless connections. In some embodiments, access point 128 may be co-located with patient 14 (FIG. 1) and may comprise one or more programming units and/or computing devices (e.g., one or more monitoring units) that may perform various functions and operations described herein. For example, access point 128 may include a home-monitoring unit that is co-located with patient 14 and that may monitor the activity of IMD 16.

During operation, IMD 16 may collect, measure, and store various forms of diagnostic data. For example, as described previously, IMD 16 may collect or measure ventricular pressure data and ventricular, or atrial, EGM data. In certain cases, IMD 16 may directly analyze collected diagnostic data and generate any corresponding reports or alerts. In some cases, however, IMD 16 may send diagnostic data to programmer 24 and/or external device 132, either wirelessly or via access point 128 and network 130, for remote processing and analysis. For example, programmer 24 and/or external device 132 may analyze the diagnostic data to determine that the value of a myocardial performance index has crossed a threshold, or that there has been a loss of ventricular stimulation capture. In these cases, programmer 24 and/or external device 132 may generate one or more alerts, or reports, indicating the condition of patient 14 (FIG. 1). In some cases, IMD 16 may adjust the electrical stimulation therapy that is provided to patient 14 upon detection (either by IMD 16 or by an external device, such as programmer 24 and/or device 132) of loss of ventricular capture.

IMD 16 may provide external device 132 with collected diagnostic data via access point 128 and network 130. External device 132 includes one or more processors 133. In some cases, external device 132 may request such data, and in some cases, IMD 16 may automatically or periodically provide such data to external device 132. Upon receipt of the diagnostic data via input/output device 131, external device 132 is capable of analyzing the data and generating reports or alerts. One or more of computing devices 134A-134N may access reports or alerts through network 130 and display the reports or alerts to users of computing devices 134A-134N. In some cases, external device 132 may automatically send information via input/output device 131 to one or more of computing devices 134A-134N as an alert, such as an audio, visual, or sensing (e.g., vibration-based) alert. In some cases, external device 132 may send information to another device, such as programmer 24, either automatically or upon request. In some cases, external device 132 may display information to a user via input/output device 131.

In one example, external device 132 may comprise a secure storage site for diagnostic information that has been collected from IMD 16 and/or programmer 24. In this embodiment, network 130 may comprise an Internet network, and trained professionals, such as clinicians, may use computing devices 134A-134N to securely access stored diagnostic data on external device 132. For example, the trained professionals may need to enter usernames and passwords to access the stored information on external device 132. In one embodiment, external device 132 may be a CareLink® server provided by Medtronic, Inc., of Minneapolis, Minn.

FIG. 7 is a timing diagram providing an overview of an example mode of operation of IMD 16 to determine an estimate of a myocardial performance index. FIG. 7 includes EGM signal 170 representative of the electrical activity in right ventricle 28 of heart 12 (FIGS. 1. and 2), and also includes right ventricle (RV) pressure signal 172 representative of the fluid pressure in right ventricle 28 of heart 12. FIG. 7 also includes first derivative dP/dt signal 174 derived by IMD 16.

R-wave 176 in EGM signal 170 represents ventricular depolarization of heart 12 (FIGS. 1 and 2), which marks start time 178 of the ventricular contraction of right ventricle 28. Upon the occurrence of R-wave 176, pressure 172 in right ventricle 28 is at a minimum pressure 180, which is often referred to as the RV end diastolic pressure. In some instances, the start time 178 of the ventricular contraction of right ventricle 28 may be determined without necessarily utilizing EGM signal 170. In these instances, IMD 16 may monitor and/or analyze pressure 172 in right ventricle 28 and determine time 178 based upon a determination of minimum pressure 180. Following ventricular depolarization, pressure 172 in right ventricle 28 increases, eventually reaching its peak pressure 182.

For a brief period at the start of ventricular contraction, no blood leaves right ventricle 28 (FIGS. 1 and 2), and the contraction is isovolumetric. During this isovolumetric contraction, the tricuspid valve at the entry of right ventricle 28 is closed by backward pressure differential forces. The pulmonary valve at the exit of right 28 ventricle is likewise closed, as pressure 172 in right ventricle 28 is insufficient to force blood through it. Consequently, this isovolumetric contraction causes the blood in right ventricle 28 to undergo increasing pressure 172.

At time 184, pressure 172 in right ventricle 28 (FIGS. 1 and 2) overcomes the pressure in the pulmonary artery, drives the pulmonary valve open, and ejects blood from right ventricle 28 into the pulmonary artery. At this time, the pressure in the right ventricle 28 is equal to the pressure in the pulmonary artery. When the pulmonary valve opens, contraction is no longer isovolumetric. Pressure 172 in right ventricle 28, although still increasing due to ventricular contraction, now increases at a slower rate. As a result, an inflection point in RV pressure signal 172 occurs at time of valve opening 184. This pressure at the inflection point, labeled 186, may be referred to as the estimated pulmonary artery diastolic pressure (ePAD). Because the slope of RV pressure signal 172 is at its maximum positive value at the inflection point, positive peak 188 of dP/dt signal 174 corresponds to the inflection point, or time 184 of the pulmonary valve opening.

After peaking at pressure 182, RV pressure 172 begins to decrease due to the continued ejection of blood from right ventricle 28 (FIGS. 1 and 2) into the pulmonary arteries. At the time 190 of the pulmonary valve closing, the pressure in right ventricle 28 continues to decrease due to relaxation of right ventricle 28. This continued decrease in pressure, however, occurs at a slower rate. Thus, there is a second inflection point in RV pressure signal 172 at the time of valve closing 190. Because the slope of RV pressure signal 172 is at its maximum negative value at the second inflection point, negative peak 192 of dP/dt signal 174 corresponds to time 190 of the pulmonary valve closing.

From these values, a pre-ejection interval (PEI) can be computed, such as by IMD 16, as the interval between the start time 178 of the ventricular contraction and time 184 of the pulmonary valve opening, as is shown in FIG. 7. A systolic time interval (STI) can be computed as the interval between the start time 178 of ventricular contraction and time 190 of the pulmonary valve closing. Finally a value of an estimated myocardial performance index (eMPI) can be computed as a numerical factor, such as two, times the PEI divided by a difference between the STI and the PEI, as shown in the formula of FIG. 7. Although shown operating in right ventricle 28 (FIGS. 1 and 2), IMD 16 may also have sensors for measuring blood pressure within left ventricle 32 (FIGS. 1 and 2).

In one embodiment, IMD 16 is capable of continually calculating a value of the eMPI over time. Based upon noteworthy changes in the eMPI value over time, or based upon individual noteworthy values of the eMPI at any given time, IMD 16 may be able to monitor the capture by electrical stimulation of one or more ventricles, and may be able to detect a loss of capture (such as may be due to lead dislodgement) within the one or more ventricles. For example, based upon RV pressure and EGM data collected and shown in FIG. 7 for right ventricle 28 (FIGS. 1 and 2), IMD 16 may be able to detect a loss of capture of electrical stimulation by left ventricle 32 (FIGS. 1 and 2). In such fashion, IMD 16 may perform capture loss management to determine whether applied stimulation is properly causing contraction of a ventricle.

The detection loss of stimulation capture (such as may be due to lead dislodgement) may be of particular value in cardiac resynchronization therapy (CRT), which often relies on synchronous pacing to improve symptoms within patients having heart conditions. For example, a loss of left ventricular capture may lead to a loss of bi-ventricular and synchronous pacing, and a loss of left ventricular capture may have a more prominent effect during CRT. Upon detection of loss of stimulation capture within a ventricle, such as the left ventricle, IMD 16 may automatically be capable of adjusting the delivery of electrical stimulation therapy, such as by increasing pacing amplitude or pulse width, to account for the loss of stimulation capture.

In certain cases, IMD 16 may regularly send EGM and pressure collection or measurement data to an external device, such as programmer 24 or external device 132 (FIG. 6). The programmer or other external device may be capable of analyzing the received data to detect a loss of stimulation capture within one or more ventricles of patient 14 (FIG. 1). In these cases, the programmer or other external device may generate a warning, or report, that is communicated to a clinician. The clinician may then take appropriate action, and may become aware of any issues that may need to be resolved within the operation of IMD 16. For example, a clinician may direct programmer 24 to adjust the delivery of electrical stimulation therapy that is provided by IMD 16 to patient 14, e.g., increase pacing amplitude or pulse width.

In order to detect a ventricular loss of stimulation capture, such as may be due to a lead dislodgment, with respect to applied stimulation, IMD 16 (or, in some cases, an external device such as device 132 or programmer 24 in FIG. 6)) may analyze the calculated values of eMPI and monitor for noticeable changes. In particular, IMD 16 may monitor for sudden or marked changes in the values of eMPI, particularly when IMD 16 delivers bi-ventricular pacing during CRT. For example, IMD 16 may compare the eMPI to a determined or preconfigured threshold value. If the value of the eMPI changes in a noticeable way, the change may indicate that IMD 16 has effectively changed to single-ventricle pacing mode. If IMD 16 has been previously programmed to deliver bi-ventricular pacing for CRT, such an indication of a change to a single-ventricle pacing mode (based upon a noticeable change in the value of the eMPI) may indicate a loss of ventricular capture of applied stimulation.

For example, if, such as in FIG. 7, IMD 16 collects or measures pressure and EGM data for right ventricle 28 (FIGS. 1 and 2) during bi-ventricular pacing, and subsequently detects a marked decrease in the value of the eMPI, IMD 16 may determine that it has effectively entered into a right-ventricle only pacing mode. Such a determination may cause IMD 16 to detect a possible loss of capture of left ventricular pacing within left ventricle 32 (FIGS. 1 and 2).

In some cases, IMD 16 may identify a possible loss of capture of left ventricular pacing within left ventricle 32 (FIGS. 1 and 2) based upon a comparison of multiple determined values of the eMPI over time. For example, IMD 16 may compute two distinct values of the eMPI at two different points in time, based upon pressure and EGM data for right ventricle 28 (FIGS. 1 and 2), and then compare these two distinct values. If the difference between the two values exceeds or falls below a determined threshold value, IMD 16 may identify a possible loss of capture within left ventricle 32.

In some cases, IMD 16 may identify a possible loss of capture of left ventricular pacing within left ventricle 32 (FIGS. 1 and 2) based upon individual values of the eMPI at particular points in time. For example, IMD 16 may compute a value of the eMPI at any point in time, based upon pressure and EGM data for right ventricle 28 (FIGS. 1 and 2), and compare this value to a determined threshold value. If the computed value of the eMPI exceeds or falls below this threshold value, IMD 16 may identify a possible loss of capture within left ventricle 32. Thus, IMD 16 is capable of determining whether electrical stimulation captured left ventricle 32 based upon individual computed values of the eMPI or upon differences between computed values of the eMPI over time. In one embodiment, IMD 16 may be preconfigured to store one or more threshold values that may be used during the analysis of computed values of the eMPI. In some cases, these threshold values may be modified within IMD 16, such as by a user of programmer 24 (for example), to modify the operation of IMD 16.

In one aspect, IMD 16 may analyze computed values of the eMPI to identify any sudden to noticeable decreases in these values over time. Upon identification of any such decreases in the values of the eMPI, IMD 16 may determine that there is a possible loss of capture within left ventricle 32 (FIGS. 1 and 2).

FIG. 8 is a timing diagram providing an overview of another example mode of operation of IMD 16 to determine a value of a myocardial performance index (MPI). In this example, IMD 16 (or an external device, such as programmer 24 or device 132 in FIG. 6) is capable of detecting a time 191 at which the pressure 172 in right ventricle 28 reaches a minimum pressure 193, which may be referred to as an RV diastolic pressure. This point on the RV pressure signal occurs after the time 190 when the pulmonary valve has closed, but prior to the right ventricle filling, and can be referred to as the relaxation phase of the cardiac cycle. The occurrence of the RV diastolic pressure 193 at time 191 may be detected by applying any peak (or valley) detection algorithm to pressure signal 172.

From these values, a post-ejection interval (PEI2) can be computed, such as by IMD 16, as the interval between the time 190 of the pulmonary valve closing and the time 191 of the RV pressure 172 reaching a minimum pressure 193. During this time, the pressure in right ventricle 28 continues to decrease due to relaxation of right ventricle 28 (FIGS. 1 and 2). A value of the MPI may then be directly computed, as shown in FIG. 8, as the sum of the pre-ejection interval and the post-ejection interval, divided by a difference between the systolic time interval and the pre-ejection interval (which may be referred to as the ejection interval).

Similar to the use of the eMPI values described with reference to FIG. 7, IMD 16 may use the computed values of the MPI, from the data shown in FIG. 8, to identify a possible condition, such as loss of capture of left ventricular pacing, based upon the calculated values of the MPI. In some cases, IMD 16 may determine whether electrical stimulation has been captured by a ventricle based upon a comparison of multiple determined values of the MPI over time, such as by comparing a difference of first and second values to a threshold. In some cases, IMD 16 may determine whether electrical stimulation captured a ventricle based upon a comparison of individual values of the MPI to a threshold value.

Figure 9:
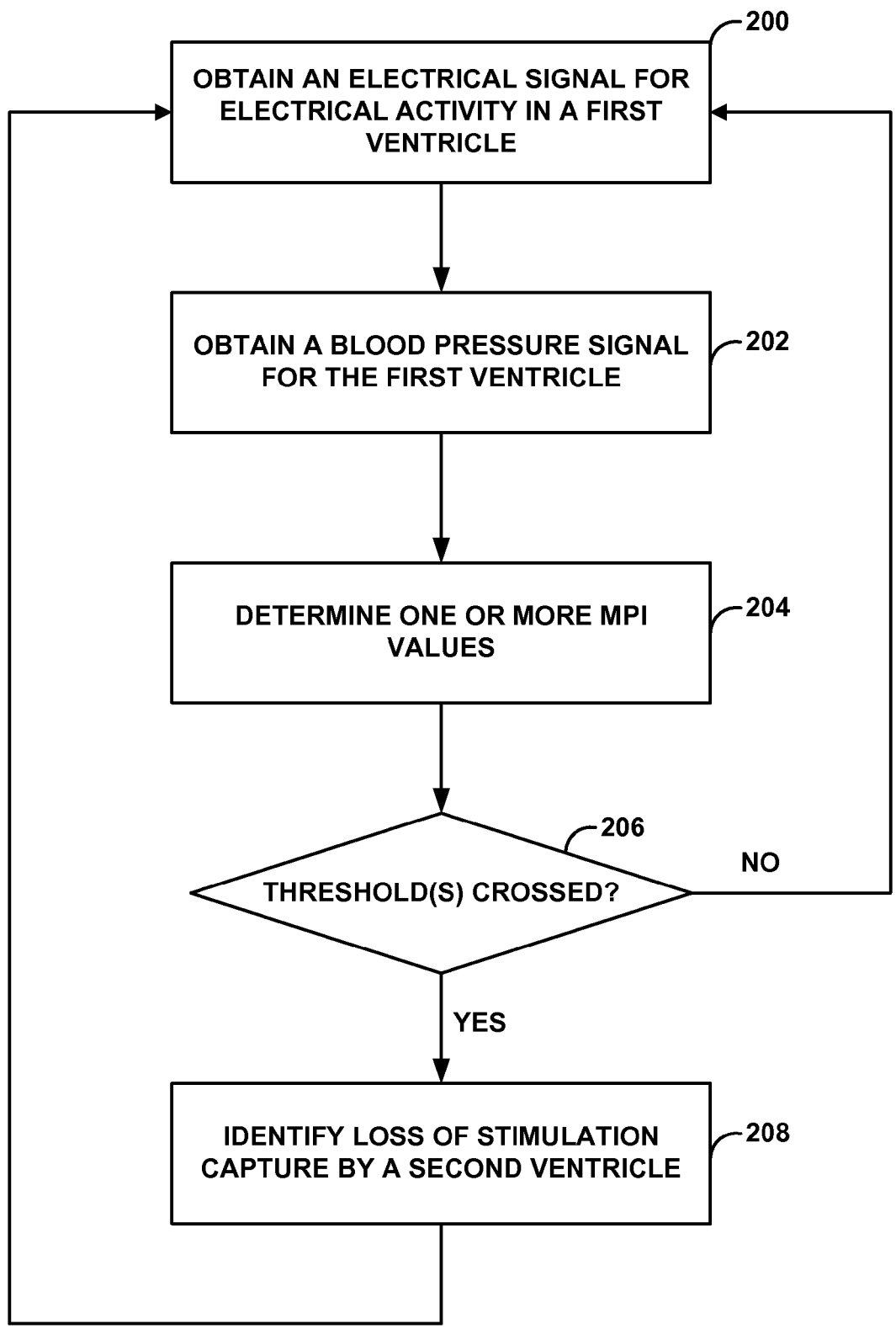
FIG. 9 is a flow diagram illustrating an example method that may be performed by one or more devices, such as by the IMD, programmer, and/or external device, shown in FIGS. 1-6, to identify whether stimulation captured a ventricle of a patient's heart.

FIG. 9 is a flow diagram illustrating an example method that may be performed by one or more devices, such as by IMD 16, programmer 24, and/or external device 132 (FIG. 6), to determine whether electrical stimulation has captured a ventricle of a patient's heart, according to one embodiment. For purposes of illustration only, it will be assumed that the method shown in FIG. 9 is performed by IMD 16.

IMD 16 may obtain an electrical signal representative of electrical activity in the first ventricle of patient 14 (200). For example, IMD 16 may use electrodes 40 and 42 to obtain EGM data for right ventricle 28. IMD 16 may then obtain a blood pressure signal for a first ventricle of patient 14 (202), such as for right ventricle 28. IMD 16 may obtain the blood pressure signal from pressure sensor 38 (FIG. 2).

IMD 16 may determine (e.g., through use of its processor 80) at least one value of a myocardial performance index based upon the blood pressure signal within the first ventricle (204), and determine if the at least one value, or a difference between two determined values, crosses one or more thresholds (206). If not, IMD 16 continues to obtain electrical signals and blood pressure signals for the first ventricle. If, however, one or more thresholds are crossed, as described in more detail below, IMD 16 identifies loss of stimulation capture of a second, different ventricle (e.g., left ventricle 32) of patient 14 based upon the at least one value of the myocardial performance index (208).

In some cases, IMD 16 may determine the at least one value of the myocardial performance index by determining a first value of the myocardial performance index based upon the blood pressure signal (or based upon the blood pressure signal and the electrical signal), and determining a second value of the myocardial performance index based upon the blood pressure signal (or based upon the blood pressure signal and the electrical signal). IMD 16 may determine whether electrical stimulation captured the second, different ventricle by comparing the first value of the myocardial performance index to the second value of the myocardial performance index. For example, IMD 16 may determine if a difference between the first value and the second value exceeds or falls below a threshold value, such as a threshold value that may be stored in memory 82 of IMD 16 (FIG. 4).

As described previously, IMD 16 may calculate a value of a myocardial performance index based upon values of a pre-ejection interval and a systolic time interval. Thus, in some instances, IMD 16 may determine the at least one value of the myocardial performance index by determining at least one pre-ejection interval and at least one systolic time interval based upon the blood pressure signal (or based upon the blood pressure signal and the electrical signal), and calculating at least one estimated value of the myocardial performance index based upon the at least one pre-ejection interval and the at least one systolic time interval (e.g., eMPI, as discussed previously).

In some instances, IMD 16 may determine post-ejection intervals (such as shown in the example of FIG. 8). In these instances, IMD 16 may determine the at least one value of the myocardial performance index by determining at least one post-ejection interval based upon the blood pressure signal, and calculating the at least one value of the myocardial performance index based upon the at least one pre-ejection interval, the at least one systolic time interval, and the at least one post-ejection interval (e.g., MPI, as discussed previously).

In some cases, IMD 16 may provide a warning signal when the at least one value of the myocardial performance index exceeds or falls below a threshold value, such as by sending a warning or alert to programmer 24 (FIG. 6). In some cases, IMD 16 may provide a therapy adjustment signal to patient 14 (FIG. 1), such as by activation of stimulation generator 84 (FIG. 4), when the at least one value of the myocardial performance index exceeds or falls below the threshold value. Stimulation generator 84 may alter, or modify, a parameter of the electrical stimulation (e.g., amplitude, frequency, pulse width) that is applied to the second, different ventricle (e.g., left ventricle 32) of patient 14.

Figure 10:
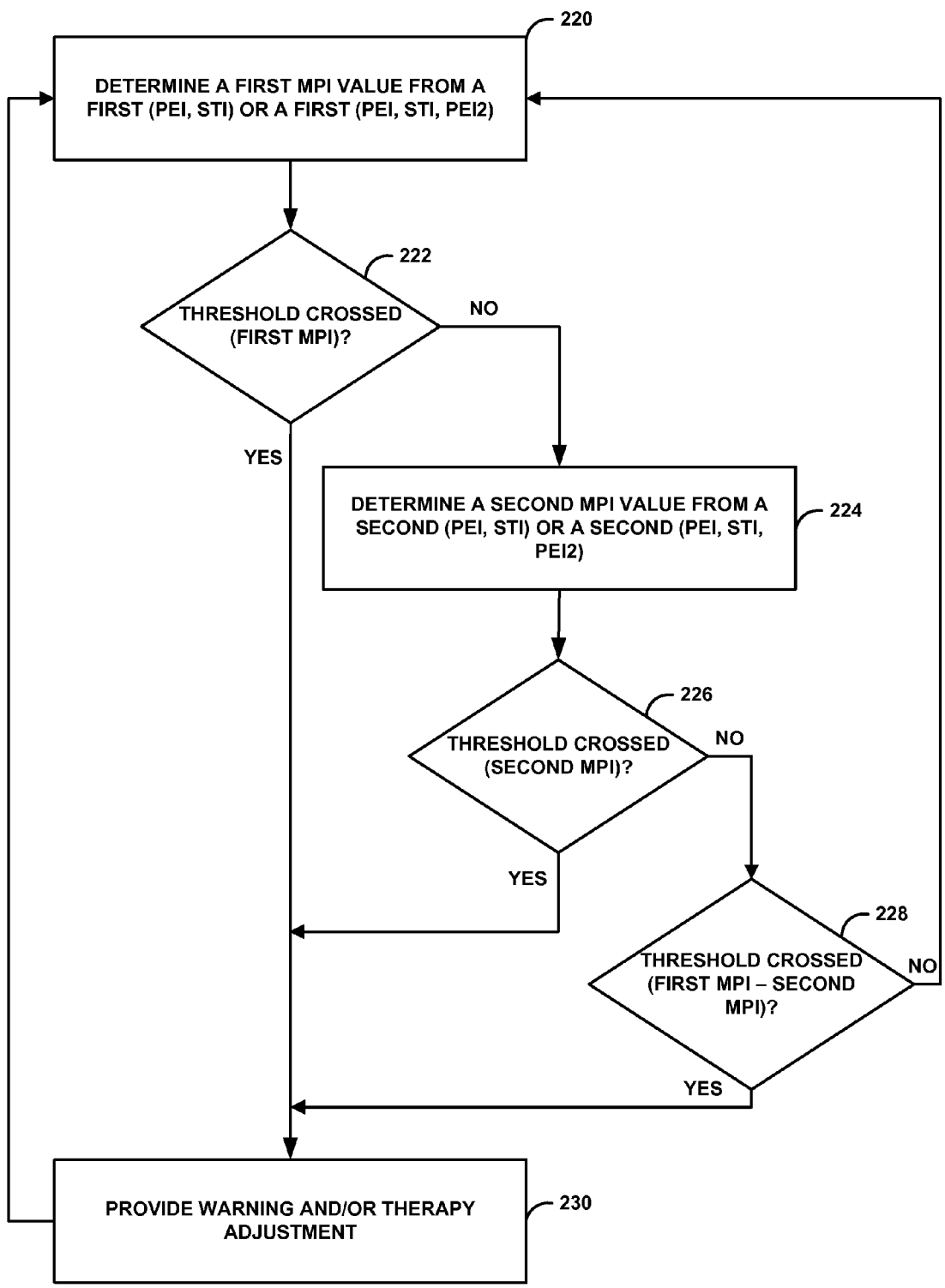
FIG. 10 is a flow diagram illustrating an example method that may be performed by one or more devices, such as by the IMD, programmer, and/or external device, shown in FIGS. 1-6, to determine if one or more values of a myocardial performance index, or difference between such values, cross one or more thresholds.

FIG. 10 is a flow diagram illustrating an example method that may be performed by one or more devices, such as by IMD 16, programmer 24, and/or external device 132 (FIG. 6), to determine if one or more values of a myocardial performance index (e.g., eMPI or MPI), or difference between such values, cross one or more thresholds, according to one embodiment. For purposes of illustration only, it will be assumed that the method shown in FIG. 10 is performed by IMD 16.

As described previously, in reference to FIG. 9, IMD 16 may determine one or more values of a myocardial performance index based upon the blood pressure signal (or based upon the blood pressure signal and the electrical signal) for the first ventricle. FIG. 10 illustrates that IMD 16 may determine multiple such values, and compare each value to a threshold to identify a possible condition of the second (e.g., left) ventricle. In addition, IMD 16 may compare a difference between two determined values to another threshold to identify a possible condition. As a result, IMD 16 is capable of analyzing individual values of the myocardial performance index, as well as differences between values, to identify any possible conditions, such as a loss of ventricular capture of applied stimulation.

As shown in FIG. 10, IMD 16 may determine a first value of a myocardial performance index from a first pre-ejection interval and a first systolic time interval, or from a first pre-ejection interval, a first systolic time interval, and a first post-ejection interval (220). IMD 16 then determines whether the first value crosses (e.g., exceeds or falls below) a first threshold value (222). This first threshold value may be stored in memory 82 of IMD 16 (FIG. 4), and may be used when analyzing individual values of the myocardial performance index. If the first value crosses the first threshold, IMD 16 may identify a possible condition of the second (e.g., left) ventricle by providing a warning signal and/or a therapy adjustment to patient 14 (230).

If the first value, however, does not cross the first threshold, IMD 16 determines a second value of the myocardial performance index from a second pre-ejection interval and a second systolic time interval, or from a second pre-ejection interval, a second systolic time interval, and a second post-ejection interval (224). IMD 16 then determines whether the second value crosses (e.g., exceeds or falls below) a second threshold value (226). This second threshold may, in some cases, equal the first threshold. If the second value crosses the second threshold, IMD 16 may identify a possible condition of the second (e.g., left) ventricle by providing a warning signal and/or a therapy adjustment to patient 14 (230).

If the second value, however, does not cross the second threshold, IMD 16 determines whether a difference between the first and second values of the myocardial performance index crosses a third threshold (228). This third threshold value may comprise a different value than the first and second threshold values used during analysis of the individual values of the myocardial performance index. In some cases, this third threshold value may be determined, or configured, in order to detect noticeable or marked changes in values of the myocardial performance index. If the difference between the first and second values of the myocardial performance index crosses (e.g., exceeds or falls below) the third threshold, IMD 16 may identify a possible condition of the second (e.g., left) ventricle by providing a warning signal and/or a therapy adjustment to patient 14 (230).

The techniques described in this disclosure, including those attributed to IMD 16, programmer 24 (FIGS. 1 and 6), or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples of the disclosure have been described. However, a person of ordinary skill in the art will understand that various modifications may be made to the described examples without departing from the scope of the claims. For example, although described herein primarily with reference to detecting loss of stimulation capture in the context of cardiac resynchronization therapy or other bi-ventricular pacing therapies, the techniques described herein may be used to detect loss of stimulation capture by a ventricle when the ventricle is the only paced ventricle. Thus, the various examples described herein, as well as other examples, are within the scope of the following claims.

The invention claimed is:

1. A method comprising:
    obtaining, from a pressure sensor that monitors pressure in a first ventricle of a heart of a patient, a blood pressure signal for the first ventricle, wherein the blood pressure signal is representative of the pressure in the first ventricle; and
    determining whether electrical stimulation, which is delivered to a second ventricle of the heart of the patient, captured the second ventricle based upon the blood pressure signal for the first ventricle but not upon a blood pressure signal for the second ventricle, the second ventricle being different from the first ventricle.

2. The method of claim 1, wherein the first ventricle comprises a right ventricle, and wherein the second ventricle comprises a left ventricle.

3. The method of claim 1, further comprising determining at least one value of a myocardial performance index based upon the blood pressure signal for the first ventricle, and wherein determining whether electrical stimulation captured the second ventricle comprises determining whether the electrical stimulation captured the second ventricle based upon the at least one value of the myocardial performance index.

4. The method of claim 3, wherein:
    determining the at least one value of the myocardial performance index comprises determining a first value and a second value of the myocardial performance index based upon the blood pressure signal; and
    determining whether the electrical stimulation captured the second ventricle comprises comparing the first and second values of the myocardial performance index, and determining whether the electrical stimulation captured the second ventricle based on the comparison.

5. The method of claim 4, wherein comparing the first and second values of the myocardial performance index comprises determining if a difference between the first value and the second value exceeds or falls below a threshold value.

6. The method of claim 4, further comprising:
    obtaining an electrical signal representative of electrical activity in the first ventricle of the patient.

7. The method of claim 6, wherein determining the first value and the second value of the myocardial performance index comprises:
    determining a first pre-ejection interval and a first systolic time interval based upon the blood pressure signal and the electrical signal;
    determining a second pre-ejection interval and a second systolic time interval based upon the blood pressure signal and the electrical signal;
    calculating a first estimated value of the myocardial performance index based upon the first pre-ejection interval and the first systolic time interval; and
    calculating a second estimated value of the myocardial performance index based upon the second pre-ejection interval and the second systolic time interval.

8. The method of claim 6, wherein determining the first value and the second value of the myocardial performance index comprises:
    determining a first pre-ejection interval and a first systolic time interval based upon the blood pressure signal and the electrical signal;
    determining a second pre-ejection interval and a second systolic time interval based upon the blood pressure signal and the electrical signal;
    determining a first post-ejection interval based upon the blood pressure signal;

determining a second post-ejection interval based upon the blood pressure signal;

calculating the first value of the myocardial performance index based upon the first pre-ejection interval, the first systolic time interval, and the first post-ejection interval; and calculating the second value of the myocardial performance index based upon the second pre-ejection interval, the second systolic time interval, and the second post-ejection interval.

9. The method of claim 3, wherein determining the at least one value of the myocardial performance index comprises:

determining at least one pre-ejection interval and at least one systolic time interval based upon the blood pressure signal; and calculating at least one estimated value of the myocardial performance index based upon the at least one pre-ejection interval and the at least one systolic time interval.

10. The method of claim 3, wherein determining the at least one value of the myocardial performance index comprises:

determining at least one pre-ejection interval and at least one systolic time interval based upon the blood pressure signal;

determining at least one post-ejection interval based upon the blood pressure signal; and calculating the at least one value of the myocardial performance index based upon the at least one pre-ejection interval, the at least one systolic time interval, and the at least one post-ejection interval.

11. The method of claim 3, wherein determining whether the electrical stimulation captured the second ventricle comprises determining whether the at least one value of the myocardial performance index exceeds or falls below a threshold value.

12. The method of claim 11, further comprising providing a warning signal when the at least one value of the myocardial performance index exceeds or falls below the threshold value.

13. The method of claim 11, further comprising providing a therapy adjustment signal to the patient when the at least one value of the myocardial performance index exceeds or falls below the threshold value.

14. A system comprising:

a processor configured to obtain, from a pressure sensor configured to monitor pressure in a first ventricle of a heart of a patient, a blood pressure signal for the first ventricle, the blood pressure signal being representative of the pressure in the first ventricle, wherein the processor is further configured to determine whether electrical stimulation, which is delivered to a second ventricle of the heart of the patient, captured the second ventricle based upon the blood pressure signal for the first ventricle but not upon a blood pressure signal for the second ventricle, the second ventricle being different from the first ventricle.

15. The system of claim 14, further comprising:

a module configured to obtain the blood pressure signal for the first ventricle from a sensor; and a stimulation generator configured to deliver the electrical stimulation to the second ventricle.

16. The system of claim 15, wherein the module and the stimulation generator are included within an implantable medical device.

17. The system of claim 14, wherein the first ventricle comprises a right ventricle, and wherein the second ventricle comprises a left ventricle.

18. The system of claim 14, wherein the processor is further configured to determine at least one value of a myocardial performance index based upon the blood pressure signal for the first ventricle, and wherein the processor is configured to determine whether the electrical stimulation captured the second ventricle based upon the at least one value of the myocardial performance index.

19. The system of claim 18, wherein:

the processor is configured to determine the at least one value of the myocardial performance index by determining a first value and a second value of the myocardial performance index based upon the blood pressure signal; and the processor is configured to determine whether the electrical stimulation captured the second ventricle by comparing the first and second values of the myocardial performance index, and by determining whether the electrical stimulation captured the second ventricle based on the comparison.

20. The system of claim 19, wherein the processor is configured to compare the first and second values of the myocardial performance index by determining if a difference between the first value and the second value exceeds or falls below a threshold value.

21. The system of claim 19, wherein the processor is further configured to obtain an electrical signal representative of electrical activity in the first ventricle of the patient.

22. The system of claim 21, wherein the processor is configured to:

determine a first pre-ejection interval and a first systolic time interval based upon the blood pressure signal and the electrical signal;

determine a second pre-ejection interval and a second systolic time interval based upon the blood pressure signal and the electrical signal;

determine the first value of the myocardial performance index by calculating a first estimated value of the myocardial performance index based upon the first pre-ejection interval and the first systolic time interval; and determine the second value of the myocardial performance index by calculating a second estimated value of the myocardial performance index based upon the second pre-ejection interval and the second systolic time interval.

23. The system of claim 21, wherein the processor is configured to:

determine a first pre-ejection interval and a first systolic time interval based upon the blood pressure signal and the electrical signal;

determine a second pre-ejection interval and a second systolic time interval based upon the blood pressure signal and the electrical signal;

determine a first post-ejection interval based upon the blood pressure signal;

determine a second post-ejection interval based upon the blood pressure signal;

calculate the first value of the myocardial performance index based upon the first pre-ejection interval, the first systolic time interval, and the first post-ejection interval; and calculate the second value of the myocardial performance index based upon the second pre-ejection interval, the second systolic time interval, and the second post-ejection interval.

24. The system of claim 18, wherein the processor is further configured to:

determine at least one pre-ejection interval and at least one systolic time interval based upon the blood pressure signal; and determine the at least one value of the myocardial performance index by calculating at least one estimated value of the myocardial performance index based upon the at least one pre-ejection interval and the at least one systolic time interval.

25. The system of claim 18, wherein the processor is further configured to:
   determine at least one pre-ejection interval and at least one systolic time interval based upon the blood pressure signal;
   determine at least one post-ejection interval based upon the blood pressure signal; and
   calculate the at least one value of the myocardial performance index based upon the at least one pre-ejection interval, the at least one systolic time interval, and the at least one post-ejection interval.

26. The system of claim 18, wherein the processor is configured to determine whether the electrical stimulation captured the second ventricle by determining whether the at least one value of the myocardial performance index exceeds or falls below a threshold value.

27. The system of claim 26, wherein the processor is configured to provide a warning signal when the at least one value of the myocardial performance index exceeds or falls below the threshold value.

28. The system of claim 26, wherein the processor is configured to provide a therapy adjustment signal when the at least one value of the myocardial performance index exceeds or falls below the threshold value.

29. An implantable medical device, comprising:
   a sensor configured to monitor pressure in a first ventricle of a heart of a patient;
   a module configured to obtain a blood pressure signal for the first ventricle from the sensor, wherein the blood pressure signal is representative of the pressure in the first ventricle;
   a stimulation generator configured to deliver electrical stimulation to a second, different ventricle of the heart of the patient; and
   a processor configured to determine whether the electrical stimulation captured the second ventricle of the patient based upon the blood pressure signal for the first ventricle but not upon a blood pressure signal for the second ventricle.

30. The implantable medical device of claim 29, wherein the first ventricle comprises a right ventricle, and wherein the second ventricle comprises a left ventricle.

31. The implantable medical device of claim 29, wherein the processor is further configured to determine at least one value of a myocardial performance index based upon the blood pressure signal for the first ventricle, and wherein the processor is configured to determine whether the electrical stimulation captured the second ventricle based upon the at least one value of the myocardial performance index.

32. The implantable medical device of claim 31, wherein:
   the processor is configured to determine the at least one value of the myocardial performance index by determining a first value and a second value of the myocardial performance index based upon the blood pressure signal; and
   the processor is configured to determine whether the electrical stimulation captured the second ventricle by comparing the first and second values of the myocardial performance index, and by determining whether the electrical stimulation captured the second ventricle based on the comparison.

33. The implantable medical device of claim 32, wherein the processor is configured to compare the first and second values of the myocardial performance index by determining if a difference between the first value and the second value exceeds or falls below a threshold value.

34. The implantable medical device of claim 32, wherein the processor is further configured to obtain an electrical signal representative of electrical activity in the first ventricle of the patient.

35. The implantable medical device of claim 34, wherein the processor is configured to:
   determine a first pre-ejection interval and a first systolic time interval based upon the blood pressure signal and the electrical signal;
   determine a second pre-ejection interval and a second systolic time interval based upon the blood pressure signal and the electrical signal;
   determine the first value of the myocardial performance index by calculating a first estimated value of the myocardial performance index based upon the first pre-ejection interval and the first systolic time interval; and
   determine the second value of the myocardial performance index by calculating a second estimated value of the myocardial performance index based upon the second pre-ejection interval and the second systolic time interval.

36. The implantable medical device of claim 34, wherein the processor is configured to:
   determine a first pre-ejection interval and a first systolic time interval based upon the blood pressure signal and the electrical signal;
   determine a second pre-ejection interval and a second systolic time interval based upon the blood pressure signal and the electrical signal;
   determine a first post-ejection interval based upon the blood pressure signal;
   determine a second post-ejection interval based upon the blood pressure signal;
   calculate the first value of the myocardial performance index based upon the first pre-ejection interval, the first systolic time interval, and the first post-ejection interval; and
   calculate the second value of the myocardial performance index based upon the second pre-ejection interval, the second systolic time interval, and the second post-ejection interval.

37. The implantable medical device of claim 31, wherein the processor is further configured to:
   determine at least one pre-ejection interval and at least one systolic time interval based upon the blood pressure signal; and
   determine the at least one value of the myocardial performance index by calculating at least one estimated value of the myocardial performance index based upon the at least one pre-ejection interval and the at least one systolic time interval.

38. The implantable medical device of claim 31, wherein the processor is further configured to:
   determine at least one pre-ejection interval and at least one systolic time interval based upon the blood pressure signal;
   determine at least one post-ejection interval based upon the blood pressure signal; and
   calculate the at least one value of the myocardial performance index based upon the at least one pre-ejection interval, the at least one systolic time interval, and the at least one post-ejection interval.

39. The implantable medical device of claim 31, wherein the processor is configured to determine whether the electrical stimulation captured the second ventricle by determining whether the at least one value of the myocardial performance index exceeds or falls below a threshold value.

40. The implantable medical device of claim 39, wherein the processor is configured to provide a warning signal when the at least one value of the myocardial performance index exceeds or falls below the threshold value.

41. The implantable medical device of claim 39, wherein the processor is configured to provide a therapy adjustment signal to the stimulation generator when the at least one value of the myocardial performance index exceeds or falls below the threshold value.

42. A computer-readable storage medium comprising instructions for causing one or more processors to:
   obtain, from a pressure sensor that monitors pressure in a first ventricle of a heart of a patient, a blood pressure signal for the first ventricle, wherein the blood pressure signal is representative of the pressure in the first ventricle; and
   determine whether electrical stimulation, which is delivered to a second ventricle of the heart of the patient, captured the second ventricle based upon the blood pressure signal for the first ventricle but not upon a blood pressure signal for the second ventricle, the second ventricle being different from the first ventricle.

43. A system comprising:
   means for obtaining, from a pressure sensor that monitors pressure in a first ventricle of a heart of a patient, a blood pressure signal for the first ventricle, wherein the blood pressure signal is representative of the pressure in the first ventricle; and
   means for determining whether electrical stimulation, which is delivered to a second ventricle of the heart of the patient, captured the second ventricle based upon the blood pressure signal for the first ventricle but not upon a blood pressure signal for the second ventricle, the second ventricle being different from the first ventricle.

* * * * *